(12) United States Patent
Yang et al.

(10) Patent No.: US 7,601,693 B2
(45) Date of Patent: Oct. 13, 2009

(54) COMPOSITION FOR TREATING CANCER AND USE THEREOF

(75) Inventors: Pan-Chyr Yang, Taipei (TW); Tse-Ming Hong, Taipei (TW); Yuh-Ling Chen, Tainan (TW); Ang Yuan, Taipei (TW); Yi-Ying Wu, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/026,537

(22) Filed: Feb. 5, 2008

(65) Prior Publication Data

US 2009/0197798 A1  Aug. 6, 2009

(51) Int. Cl.
C07K 5/12 (2006.01)
(52) U.S. Cl. .......................... 514/12; 530/317; 530/329
(58) Field of Classification Search .................. 514/12; 530/317, 329
See application file for complete search history.

(56) References Cited

U.S. PATENT DOCUMENTS

2002/0193431 A1* 12/2002 Serhan et al. ................ 514/475

OTHER PUBLICATIONS

Chen et al. (Proc. American Association of Cancer Research 2006; 47: Abstract 1632).*
Hong et al. (Clinical Cancer Research 2007; 13(16): 4759-4768).*
Kenji Shibuya et al.; Global and regional estimates of cancer mortality and incidence by site: II. results for the global burden of disease 2000; journal; Dec. 26, 2002; pp. 1-26; vol. 2, No. 37; BMC Cancer; BioMed Central Ltd.
Philip C Hoffman et al.; Lung cancer; seminar; Feb. 5, 2000; pp. 479-485; vol. 355; The Lancet.
Yok-Lam Kwong et al.; Combination Therapy With Suicide and Cytokine Genes for Hepatic Metastases of Lung Cancer; journal; Nov. 1997; pp. 1332-1337; vol. 112; Chest; The American College of Chest Physicians; Northbrook IL.
Napoleone Ferrara et al.; The biology of VEGF and its receptors; journal; Jun. 2003; pp. 669-676; vol. 9, No. 6; Nature Medicine; Nature Publishing Group.
Sergio Dias et al.; Inhibition of both paracrine and autocrine VEGF/ VEGFR-2 signaling pathways is essential to induce long-term remission of xenotransplanted human leukemias; journal; Sep. 11, 2001; pp. 10857-10862; vol. 98, No. 19; PNAS.
Matilde Murga et al.; Neuropilin-1 regulates attachment in human endothelial cells independently of vascular endothelial growth factor receptor-2; Mar. 1, 2005; pp. 1992-1995; vol. 105, No. 5; Blood; The American Society of Hematology; Washington DC.
Lee M. Ellis; The Role of Neuropilins in Cancer; Molecular Therepeutics; May 2006; pp. 1099-1107; vol. 5, No. 5; Texas.
Yi-Wen Chu et al.; Selection of Invasive and Metastatic Subpopulations from a Human Lung Adenocarcinoma Cell Line; American Journal, of Respiratory Cell and Molecular Biology; Nov. 4, 1996; pp. 353-360; vol. 17.
Jeremy J. Chen et al.; Profiling Expression Patterns and Isolating Differentially Expressed Genes by cDNA Microarray System with Colorimetry Detection; Genomics; Apr. 20, 1998; pp. 313-324; vol. 51, Article No. GE985354; Taiwan.
Clinton F. Mountain; Revisions in the International System for Staging Lung Cancer; Chest; 1997; pp. 1710-1717; vol. 111, No. 6; American College of Chest Physicians; Illinois.
Christian A. Heid et al.; Real Time Quantitative PCR; Genome; 1998; pp. 986-994; Cold Spring Harbor Laboratory Press; California.
Shay Soker et al.; VEGF165 Mediates Formation of Complexes Containing VEGFR-2 and Neuropilin-1 That Enhance VEGF165-Receptor Binding; Journal of Cellular Biochemistry; 2002; pp. 357-368; vol. 85; Massachusetts.
Ming-Tsan Lin et al.; Cyclooxygenase-2 Inducing Mcl-1-dependent Survival Mechanism in Human Lung Adenocarcinoma CL1.0 Cells; The Journal of Biochemistry; 2001; pp. 48997-49002; vol. 276, No. 52; USA.
Masahito Tamura et al.; Inhibition of Cell Migration, Spreading, and Focal Adhesions by Tumor Suppressor PTEN; Journal; 1998; pp. 1614-1617; vol. 280; Science; American Advancement of Science; Washington DC.
Yuh-Ling Chen et al., Neuropilin-1 and Lung Cancer Progression: potential role of targeting neuropilin-1 as an anti-tumor strategy, poster presented at the AACR (American Association for Cancer Research) meeting in 2006, Washington DC, USA.

* cited by examiner

*Primary Examiner*—Brandon J Fetterolf
(74) *Attorney, Agent, or Firm*—WPAT, P.C.; Anthony King; Kay Yang

(57) ABSTRACT

The present invention provides a cyclic peptide containing RRXR motif. The present invention also provides a composition comprising the said cyclic peptide and a pharmaceutical acceptable carrier. The present invention further provides a method for treating cancer.

2 Claims, 11 Drawing Sheets

A

N: non-silencing siRNA

B

G

H

A

1. NT
2. VEGF (1.3nM)
3. VEGF + sNRP1 (1nM)
4. VEGF + sNRP1 (10nM)
5. VEGF + sNRP1 (20nM)
6. VEGF + sNRP1 (50nM)

B

C a  SF+1.3nM VEGF b  SF+1.3nM VEGF + 10nM sNRP1

D

E

SEQUENCE LISTING

```
<160> NUMBER OF SEQ ID NOS: 23

<210> SEQ ID NO 1
<211> LENGTH: 9
<212> TYPE: PRT
<213> ORGANISM: Artificial
<220> FEATURE:
<223> OTHER INFORMATION: synthesized by Digitalgene (Taiwan)
<220> FEATURE:
<221> NAME/KEY: UNSURE
<222> LOCATION: (1)..(9)

<400> SEQUENCE: 1

Cys Arg Arg Pro Arg Met Leu Thr Cys
1               5

<210> SEQ ID NO 2
<211> LENGTH: 9
<212> TYPE: PRT
<213> ORGANISM: Artificial
<220> FEATURE:
<223> OTHER INFORMATION: synthesized by Digitalgene (Taiwan)
<220> FEATURE:
<221> NAME/KEY: UNSURE
<222> LOCATION: (1)..(9)

<400> SEQUENCE: 2

Cys Arg Ser Arg Arg Ile Arg Leu Cys
1               5

<210> SEQ ID NO 3
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 3
ggcacactca gggtcaaact                                              20

<210> SEQ ID NO 4
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 4
atgccaacag gcacagtaca                                              20
```

```
<210> SEQ ID NO 5
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 5
aggaacttgt cccagcaaaa                                           20

<210> SEQ ID NO 6
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 6
atgcagctca gacactcctg                                           20

<210> SEQ ID NO 7
<211> LENGTH: 23
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(23)

<400> SEQUENCE: 7
ctggcatggt cttctgtgaa gca                                       23

<210> SEQ ID NO 8
<211> LENGTH: 22
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(22)

<400> SEQUENCE: 8
aataccagtg gatgtgatgc gg                                        22

<210> SEQ ID NO 9
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 9
aacctggaga gcaagaacca                                           20

<210> SEQ ID NO 10
<211> LENGTH: 20
<212> TYPE: DNA
```

-continued

```
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 10
gacttggtga aggtggagga                                               20

<210> SEQ ID NO 11
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 11
tactgataac ttcttgcttc                                               20

<210> SEQ ID NO 12
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 12
gtatggaacc tggctaactg                                               20

<210> SEQ ID NO 13
<211> LENGTH: 21
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(21)

<400> SEQUENCE: 13
gtgaatgcag accaaagaaa g                                             21

<210> SEQ ID NO 14
<211> LENGTH: 18
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(18)

<400> SEQUENCE: 14
aaaccctgag ggaggctc                                                 18

<210> SEQ ID NO 15
<211> LENGTH: 19
<212> TYPE: DNA
<213> ORGANISM: Artificial
<220> FEATURE:
<223> OTHER INFORMATION: primer synthesis
<220> FEATURE:
```

-continued

```
<221> NAME/KEY: misc_binding
<222> LOCATION: (1)..(19)

<400> SEQUENCE: 15
cagaaaagcc cacggtcat                                          19

<210> SEQ ID NO 16
<211> LENGTH: 23
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(23)

<400> SEQUENCE: 16
cagccaaatt cacagttaaa acc                                     23

<210> SEQ ID NO 17
<211> LENGTH: 31
<212> TYPE: DNA
<213> ORGANISM: Artificial
<220> FEATURE:
<223> OTHER INFORMATION: TaqMan probe
<220> FEATURE:
<221> NAME/KEY: misc_binding
<222> LOCATION: (1)..(31)

<400> SEQUENCE: 17
acagcaccat acaatcagag tttcccacat a                            31

<210> SEQ ID NO 18
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 18
cacgaaccac ggcactgatt                                         20

<210> SEQ ID NO 19
<211> LENGTH: 22
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(22)

<400> SEQUENCE: 19
ttttcttgct gccagtctgg ac                                      22

<210> SEQ ID NO 20
<211> LENGTH: 25
<212> TYPE: DNA
<213> ORGANISM: Artificial
<220> FEATURE:
<223> OTHER INFORMATION: TaqMan probe
<220> FEATURE:
<221> NAME/KEY: misc_binding
<222> LOCATION: (1)..(25)

<400> SEQUENCE: 20
```
tgtgcacagg agccaagagt gaaga          25

<210> SEQ ID NO 21
<211> LENGTH: 21
<212> TYPE: DNA
<213> ORGANISM: Artificial
<220> FEATURE:
<223> OTHER INFORMATION: coding siRNA
<220> FEATURE:
<221> NAME/KEY: misc_feature
<222> LOCATION: (1)..(21)

<400> SEQUENCE: 21
aattctccga acgtgtcacg t          21

<210> SEQ ID NO 22
<211> LENGTH: 21
<212> TYPE: DNA
<213> ORGANISM: Artificial
<220> FEATURE:
<223> OTHER INFORMATION: coding siRNA
<220> FEATURE:
<221> NAME/KEY: misc_feature
<222> LOCATION: (1)..(21)

<400> SEQUENCE: 22
aacacctagt ggagtgataa a          21

<210> SEQ ID NO 23
<211> LENGTH: 21
<212> TYPE: DNA
<213> ORGANISM: Artificial
<220> FEATURE:
<223> OTHER INFORMATION: coding siRNA
<220> FEATURE:
<221> NAME/KEY: misc_feature
<222> LOCATION: (1)..(21)

<400> SEQUENCE: 23
aacagccttg aatgcactta t          21

COMPOSITION FOR TREATING CANCER AND USE THEREOF

FIELD OF THE INVENTION

The present invention relates to a cyclic peptide containing RRXR motif.

The present invention also relates to a composition comprising the said cyclic peptide and a pharmaceutical acceptable carrier.

The present invention further relates to a method for treating cancer.

BACKGROUND OF THE INVENTION

Neuropilin 1 (NRP1) was originally identified as a neuronal semaphorin 3A receptor that mediates axonal extension during embryonic development. It was later discovered to be present in endothelial cells, mediating angiogenesis during development and in lung cells, controlling lung branching during development (Roche J, et al., Adv Exp Med Biol 2002, 515:103-114). NRP1 is a type I transmembrane glycoprotein and a coreceptor for two extracellular ligands, semaphorins/collapsins, and vascular endothelial growth factor (VEGF; Ferrara N, et al., Nat Med 2003, 9:669-976). VEGF mediates tumor angiogenesis and directly enhances tumor growth via VEGF/VEGF receptor (VEGFR) autocrine loops in tumors (Dias S, et al., Proc Natl Acad Sci USA 2001, 98:10857-10862). NRP1 forms complexes with Flt-1 (VEGFR1) and Flk-1/KDR (VEGFR2) to enhance the binding of $VEGF_{165}$ to VEGFRs and promotes $VEGF_{165}$-mediated tumor angiogenesis, cell migration, and tumorigenicity (Murga M, et al., Blood 2005, 105:1992-1999).

NRP1 has been observed in cancer cells, including PC3 prostate cancer cells and metastatic MDA-MB-231 breast cancer cells as well as several other types of tumor cells (Lee M., Mol Cancer Ther 2006, 5:1099-1107). Overexpression of NRP1 enhances tumor angiogenesis and tumor growth in vivo (Klagsbrun M, et al., Adv Exp Med Biol 2002, 515: 33-48). NRP1 expression is present in various human cancers (Ellis LM. Mol Cancer Ther 2006, 5:1099-1107) and is associated with increased tumor aggressiveness and neovascularization; however, its modes of action are not fully understood.

Lung cancer is the most common cause of cancer deaths, accounting for 17% of deaths from cancer (Shibuya K, et al., BMC Cancer 2002, 2:37). Non-small cell lung carcinoma (NSCLC) is the predominant type of lung cancer (Hoffman P C, et al., Lancet 2000, 355:479-485). Metastasis is the major cause of treatment failure and cancer deaths (Kwong Y L, et al., Chest 1997, 112: 1332-1337). The identification of metastasis enhancers and their signaling pathways may improve our understanding of the metastatic process and provide future targeted therapy for NSCLC patients.

BRIEF DESCRIPTION OF THE DRAWINGS

FIG. 3 Continued. G: cells were infected with shLuc or shNRP1 lentivirus and then selected by culture medium containing 0.75 µg/mL puromycine for 1 week. Left, Western blots of the cell lysates. Right, invasiveness of the treated cells. H: mice significantly developed more pulmonary metastatic nodules after tail vein injection with CL1-5/shLuc cells compared with CL1-5/shNRP-1cells. The lung metastatic nodules were recorded and analyzed by the Student's t test (P=0.0063).

Figure 1:
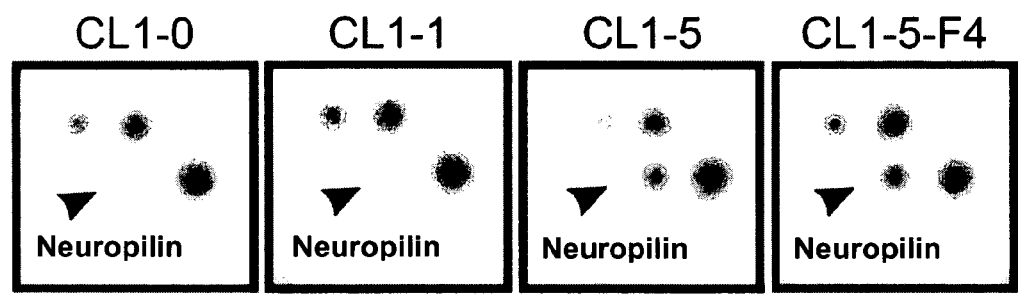
FIG. 1 shows NRP1 is up-regulated in highly invasive human lung adenocarcinoma cell lines. A: close-up views of microarray images showing NRP1 up-regulation in highly invasive CL1-5 and CL1-5-F4 cells. B: RT-PCR analysis of the differential expression of NRP1, semaphorin 3A (Sema3A), Flk-1/KDR, PLxA1, $VEGF_{165}$, and $VEGF_{121}$ in each of the CL1 sublines. The GP-like gene was used as an internal control.
Figure 1:
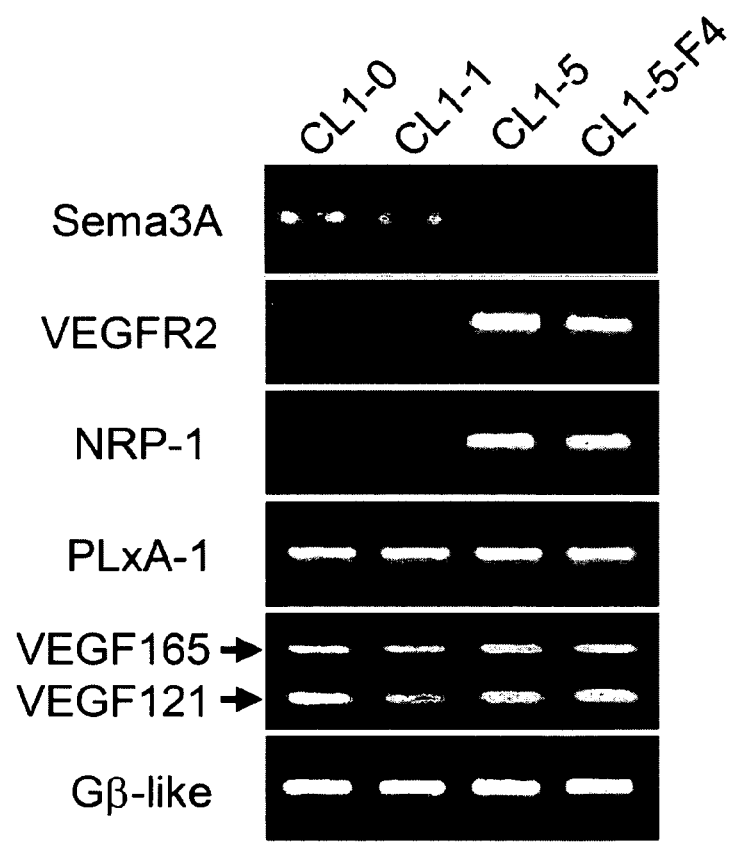

Then, the cells that had invaded the membrane were counted. Values were normalized to the relative invasion activity of the nontreated control cells. Experiments were done in triplicate, three independent times. In DG1- and DG2-treated cells, the invasion ability was statistically significantly different across the various concentrations of DG1 or DG2 by ANOVA (DG1, P<0.001; DG2, P=0.011). C: the effect of peptides on tumor angiogenesis in vivo. Immunohistochemical staining of the Matrigel plug sections with an anti-CD31 antibody showed a significant decrease in CD31-positive vessels in plugs containing DG1 peptide compared with mock-treated plugs. Original magnification, x200. The counts of microvessels surrounding the tumor nests were calculated. D: effect of peptides on tumorigenesis in vivo. Volumes of tumors from control CL1-5 cells (▲) and DG1-treated cells (■) were measured at the indicated times as described in Materials and Methods. Means and 95% CI are shown (n=5 mice per group). E: summary diagram showing that $VEGF_{165}$ can bind to NRP1 and trigger the NRP1/VEGFR2/PI3K/Akt signaling pathways and result in tumor angiogenesis, cancer cell invasion, and tumorigenesis. The synthetic peptides DG1/DG2 can specifically block this signaling pathway and may have therapeutic potential.

SUMMARY OF THE INVENTION

The present invention provides a cyclic peptide containing RRXR motif.

The present invention also provides a composition comprising the said cyclic peptide and a pharmaceutical acceptable carrier.

The present invention further provides a method for treating cancer.

DETAILED DESCRIPTION OF THE INVENTION

We identified by cDNA microarray that NRP1 expression is positively correlated with the invasion ability of cancer cells in lung cancer cell line models (Chen J J, et al., Genomics 1998, 51:313-324). However, the role of NRP1 in cancer progression in NSCLC patients is not fully understood. In the present invention, the role of NRP1 as an enhancer for cancer invasion, metastasis, and angiogenesis and its signaling pathways, prognostic significance, and therapeutic implications is elucidated.

The present invention indicates that NRP1 is an enhancer of cancer invasion and angiogenesis and is an independent predictor of cancer relapse and poor survival in NSCLC patients. Suppression of NRP1 signaling inhibits cancer invasion, tumorigenesis, angiogenesis, and in vivo metastasis. The protumorigenic effect of NRP1 involves VEGF, PI3K, and Akt pathways. Two potent synthetic anti-NRP1 peptides (DG1 and DG2), which can block NRP1 signaling pathways, inhibit tumorigenesis, cancer invasion, and angiogenesis, were identified. NRP1 is expected to be a potential biomarker for the selection of high-risk NSCLC patients for adjuvant chemotherapy, antiangiogenesis therapy, or other new targeted therapies. This allows the maximization of potential therapeutic benefits for high-risk patients and spare low-risk patients from unnecessary treatment or toxicity. In the present invention, we showed that NRP1 interacts with VEGFR2 to mediate VEGF-induced tumor invasion. VEGF mediates tumor angiogenesis and promotes migration and invasion of tumor cells by directly acting on its receptors via an endothelial cell-independent pathway. NRP1 alone has been shown to mediate breast cancer cell migration in a VEGFR2-independent manner, and in vitro studies have shown that VEGFR1 activation by VEGF-A or VEGF-B in colorectal cancer cells leads to an increase in cell migration and invasion. VEGF competes with semaphorin 3A for NRP1/plexin A1 complex binding and enhances breast carcinoma migration via an autocrine pathway. NRP1 also inhibits migration, independent of semaphorin 3A, in pancreatic adenocarcinoma cells. DG1 and DG2 specifically inhibited phosphorylation of VEGFR2 at $Tyr^{1214}$ induced by VEGF165 in a concentration-dependent manner. The role of NRP1 in enhancing tumor angiogenesis and tumor growth suggests that antagonizing NRP1 activity in tumor cells may be a feasible antitumor strategy. In the present invention, several small peptides with the consensus RRXR sequence motif specifically block NRP1 signaling and suppress cancer cell invasion, tumorigenesis, and tumor angiogenesis. The minimal NRP1-binding synthetic peptide DG1 inhibited the invasive activity and in vivo angiogenesis of cancer cells without affecting cell viability. DG1 can inhibit $VEGF_{165}$-mediated downstream signaling and VEGFR2 phosphorylation. Although no sequence homology was found between the selected peptides and $VEGF_{165}$, we found that peptides with positive net charges and a cysteine-linked cyclic conformation are essential for NRP1 binding.

NRP1 is a cancer invasion and angiogenesis enhancer. NRP1 is an independent predictor of cancer relapse and poor survival in NSCLC patients. NRP1 plays a critical role in tumorigenesis, cancer invasion, metastasis, and angiogenesis through VEGF, PI3K, and Akt pathways. NRP1 is a potential new therapeutic target in NSCLC. Synthetic anti-NRP1 peptides with conserved RRXR sequence motifs can block NRP1 signaling pathways and suppress tumorigenesis, cancer invasion, and angiogenesis.

Accordingly, the present invention provides a cyclic peptide containing RRXR motif, wherein R is arginine and X is any amino acid.

In one embodiment, the said cyclic peptide is DG1 of SEQ ID NO: 1 or DG2 of SEQ ID NO: 2.

The present invention also provides a composition comprising the cyclic peptide of claim 1 and a pharmaceutical acceptable carrier. In one embodiment, the said cyclic peptide is DG1 or DG2.

The present invention further provides a method for treating cancer, comprising administering a subject with the above composition. The cancer is breast cancer, colorectal cancer, esophageal cancer, gall bladder cancer, glioma, neuroblastoma, lung cancer, pancreatic cancer, prostate cancer. In one preferred embodiment, the cancer is lung cancer. In the most preferred embodiment, the cancer is non-small cell lung cancer.

In one embodiment, the subject is an animal. In more preferred embodiment, the subject is a mammal. In the most preferred embodiment, the subject is a human.

The cancer treatment of the present invention involves in inhibition of cancer cell invasion, tumorigenesis, and tumor angiogenesis.

EXAMPLE

The examples below are non-limiting and are merely representative of various aspects and features of the present invention.

Materials

Cells and Reagents.

Human lung cancer cell lines, CL1-0, CL1-1, CL1-5, and CL1-5-F4, were established by selection of increasingly invasive cell populations from a clonal cell line of human lung adenocarcinoma, CL1 (Chu Y W, et al., Am J Respir Cell Mol Biol 1997, 17:353-360). Human umbilical vascular endothelial cells (HUVEC) and culture media were purchased from Cell Applications, Inc. Cell culture reagents were from Invitrogen. Human VEGF165 was from PeproTech, Inc. Human anti-phospho-VEGFR2 antibody was from Calbiochem. Anti-VEGFR2 (sc-504) antibody was from Santa Cruz Biotechnology. Mouse antibody to phosphotyrosine (clone 4G10) was from Upstate Biotechnology Inc. Anti-phospho-Akt, anti-Akt antibodies, wortmannin, and LY294002 were from New England Biolabs, and other reagents were obtained from Sigma-Aldrich. Recombinant soluble NRP1 (sNRP1) protein containing His6 and c-Myc domain tags was synthesized in NIH-3T3 murine fibroblast cells. Two cyclic peptides DG1 (CRRPRMLTC) SEQ ID NO: 1 and DG2 (CRSRR-IRLC) SEQ ID NO: 2 were synthesized by Digitalgene (Taiwan). Primer sequences for reverse transcription-PCR(RT-PCR) and real-time PCR(r) analysis are shown in Table 2.

Patients and Tissue Specimens.

Sixty consecutive patients who underwent surgery for NSCLC at the National Taiwan University Hospital from Sep. 1, 1994, to Apr. 30, 1998, were included in the study. This investigation was approved by the Institutional Review Board of the National Taiwan University Hospital. None of the patients had received neoadjuvant chemotherapy or radiation therapy before surgery. Specimens of lung cancer tissue obtained at surgery were immediately snap-frozen in liquid nitrogen and stored at −80jC until use. The postsurgical pathologic stage of each tumor was classified according to the international tumor-node-metastasis classification (Mountain C F. et al., Chest 1997, 111: 1710-1717). The demographic features of the patients are shown in Table 1.

TABLE 1

Clinicopathologic characteristics of 60 NSCLC patients

| Characteristic | Low NRP1 expression patients (%), n = 30 | High NRP1 expression patients (%), n = 30 | P |
|---|---|---|---|
| Age (mean ± SD), y | 64.4 ± 11.5 | 62.1 ± 11.1 | 0.435* |
| Sex | | | |
| Male | 21 (70) | 15 (50) | 0.187[†] |
| Female | 9 (30) | 15 (50) | |
| Stage | | | |
| I and II | 20 (67) | 12 (40) | 0.069[†] |
| III and IV | 10 (33) | 18 (60) | |
| Histology | | | |
| Adenocarcinoma | 14 (47) | 22 (73) | 0.064[†] |
| Squamous | 16 (53) | 8 (27) | |

*t test.
[†]Fisher's exact test.

TABLE 2

Primer and siRNA sequence and amplicon length

| Gene | Forward primer | Reverse primer | Amplicon length |
|---|---|---|---|
| NRP1 | GGCACACTCAGGGTCAAACT (SEQ ID NO:3) | ATGCCAACAGGCACAGTACA (SEQ ID NO:4) | 455 |
| Sema3A | AGGAACTTGTCCC AGCAAAA (SEQ ID NO:5) | ATGCAGCTCAGACACTCCTG (SEQ ID NO:6) | 1190 |
| VEGFR2 | CTGGCATGGTCTTCTGTGAAGCA (SEQ ID NO:7) | AATACCAGTGGATGTGATGCGG (SEQ ID NO:8) | 793 |
| PLxA1 | AACCTGGAGAGCAAGAACCA (SEQ ID NO:9) | GACTTGGTGAAG GTGGAGGA (SEQ ID NO:10) | 602 |
| Gβ | TACTGA TAACTTCTTGCTTC (SEQ ID NO:11) | GTATGGAACCTGGCTAACTG (SEQ ID NO:12) | 304 |
| VEGF | GTGAATGCAGACCAAAGAAAG (SEQ ID NO:13) | AAACCCTGAGGGAGGCTC (SEQ ID NO:14) | 96, 228 |
| NRP1 (r) | CAGAAAAGCCCACGGTCAT (SEQ ID NO:15) | CAGCCAAATTCACAGTTAAAACC (SEQ ID NO:16) | 76 |
| | TaqMan probe, (FAM)-ACAGCACCATACAATCAGAGTTTCCCA CATA-(TAMRA). (SEQ ID NO:17) | | |

TABLE 2-continued

Primer and siRNA sequence and amplicon length

| Gene | Forward primer | Reverse primer | Amplicon length |
|---|---|---|---|
| TBP(r) | CACGAACCACGGCACTGATT (SEQ ID NO:18) | TTTTCTTGCTGCCAGTCTGGAC (SEQ ID NO:19) | 89 |
| | TaqMan probe (FAM)-TGTGCACAGGAGCCAAGAGTGAAGA-(TAMRA). (SEQ ID NO:20) | | |
| *Nonsilencing siRNA | | AATTCTCCGAACGTGTCACGT (SEQ ID NO:21) | |
| *NRP1 siRNA#1 | | AACACCTAGTGGAGTGATAAA (SEQ ID NO:22) | |
| *NRP1 siRNA#2 | | AACAGCCTTGAATGCACTTAT (SEQ ID NO:23) | |

*Desalted small interfering RNA (siRNA) duplexes were synthesized by Qiagen and were annealed following its standard protocol. siRNAs were transfected using the RNAiFect Transfection Reagent (Qiagen) according to the manufacturer's instructions.

Methods

NRP1 mRNA Expression in Tumor Specimens from NSCLC Patients.

NRP1 expression in tumors from NSCLC patients was measured by real-time quantitative RT-PCR, based on TaqMan methodology, using the ABI PRISM 7900 Sequence Detection System (Applied Biosystems; Heid C A, et al., Genome Res 1994, 6: 986-994). The relative amounts of tissue NRP1 mRNA expression were normalized with TATA-box binding protein mRNA and expressed as $-\Delta CT=[CT_{(NRP1)}-CT_{(TBP)}]$. Patients were included in the high-expression group when $-\Delta CT$ was 0.32 (the median) or greater. The primer probe sets were designed and synthesized by Applied Biosystems. The sequences of primers and small interfering RNAs (siRNA) used in this study are listed in Table 2. In Vitro invasion Assay.

A modified Boyden chamber system was used to investigate the invasive capability of CL cells treated with selected peptides, sNRP1, and siRNA of NRP1 (Chu Y W, et al., Am J Respir Cell Mol Biol 1997, 17: 353-360). The polycarbonate membranes (containing 8-μm pores) of Transwell inserts were coated with Matrigel. The cells were suspended in RPMI 1640 containing 10% NuSerum (Life Science), and $2.5 \times 10^4$ cells were placed into the upper well of each chamber. After incubation for 48 h at 37° C., the Transwell membrane was fixed with methanol for 10 min at room temperature and stained with a 50 μg/mL solution of propidium iodide (Sigma) for 30 min at room temperature. The number of cells in each membrane was counted under a microscope at a magnification of ×50 using the Analytical Imaging Station software package (Imaging Research Inc.). Each sample was assayed in triplicate.

Identification of NRP1-Binding Peptides by Phage Display.

A phage peptide library displaying cyclic random peptides (Ph.D.C. 7C from New England Biolabs) was used for biopanning of NRP1. Recombinant human sNRP1 protein was coated onto the wells of polystyrene 96-well plates and incubated with $2 \times 10^{11}$ plaque-forming units of the primary library. Bound phages were eluted with glycine-HCl (pH, 2.2) and amplified in *Escherichia coli* (ER2738). Biopanning was repeated for four rounds, with concentrations of Tween 20 in the wash solution increasing from 0.1% to 0.7%. Randomly selected phage clones from the fourth round of panning were sequenced.

Surface Plasmon Resonance.

The binding kinetics of selected peptides with NRP1 were tested using the surface plasmon resonancebased measuring system (Biacore AB) at 25° C. Recombinant NRP1 was immobilized on CM5 sensor chips by amine coupling at 400 response units using the amine coupling kit (Biacore) according to the manufacturer's instructions. Binding was detected in resonance units after injecting various concentrations of peptide at a flow rate of 30 μL/min. Sensograms of association and dissociation were recorded and analyzed using BIAevaluation software 3.0 (Biacore AB).

VEGFR Tyrosine Phosphorylation.

VEGFR2 phosphorylation was assessed as previously described (Soker S, et al., J Cell Biochem 2002, 85:357-368). Briefly, CL1-5 cells were treated with a mixture of hVEGF and sNRP1 for 30 min on ice and then at 37° C. for 7 min. Cell lysates were immunoprecipitated with anti-VEGFR2 antibodies. For Western blotting, the membranes were first probed with anti-Flk-1 antibodies and then reprobed with anti-phospho-VEGFR2 antibodies $\frac{2}{3}$(pc460) after being stripped with deblotting buffer. In the antiangiogenesis assay, HUVECs were pretreated with peptides for 10 min followed by treatment with VEGF for 5 min, and the cells were then immediately extracted with lysis buffer. Activation of Flk-1/KDR was determined by immunoblotting cell extracts with anti-Flk-1 antibodies and then reprobing with anti-phospho-VEGFR2 antibodies ($pTyr^{1214}$) after the membranes had been stripped with deblotting buffer.

Phosphoinositide-3-Kinase Activity Assay.

Phosphoinositide-3-kinase (PI3K) activities were assayed as described previously (Lin M T, et al., J Biol Chem 2001, 276: 48997-49002) with some modifications. In brief, CL1-5 cell extracts were incubated with the antiphosphotyrosine antibody and then precipitated with protein A-Sepharose. The immunocomplexes were preincubated with phosphatidylinositol-4,5-$P_2$ (Sigma), and the kinase reaction was initiated by adding 10 μCi of [$\gamma$-$^{32}$P]ATP in reaction buffer for 15 min. Phospholipids were separated by TLC and visualized by phosphorimaging.

Wound Healing.

Cell migration was measured by the in vitro scratch wound healing assay (Tamura M, et al., Science 1998, 280: 1614-1617). CL1-5 cells were transfected with 24 nmol/L siRNA-1 in 12-well plates. Twenty-four hours after transfection, cells were scratched with a yellow pipette tip and photographed 18, 21, and 24 h after the scratch. The cell migration at 0, 18, 21, and 24 h was evaluated by counting cells that had migrated from the wound edge.

Filamentous Actin Staining.

For filamentous actin (F-actin) staining, cells were seeded on coverslips in 24-well plates and allowed to attach for 24 h in medium containing 10% FCS.

The cells were fixed, washed, and permeabilized in 0.1% Triton-X. The cells were incubated for 30 min with 5 units/mL of rhodamine-conjugated phalloidin (Molecular Probe) and mounted using Fluor Save reagent (Calbiochem). The slides were analyzed using a Zeiss Axioplan 2 microscope.

Experimental Metastasis In Vivo.

Cells were washed and resuspended in PBS. Subsequently, a single-cell suspension containing $10^6$ cells in 0.1 mL of PBS was injected into the lateral tail veins of the 6-week-old severe combined immunodeficiency (SCID) mice (supplied by the animal center in the College of Medicine, National Taiwan University, Taipei, Taiwan). Mice were killed after 5 weeks. The lungs were removed, weighed, and fixed in 10% formalin for further examination of metastasis formation. The number of lung tumor colonies was counted under a dissecting microscope. All animal experiments were done in accordance with the animal guidelines at the Department of Animal Care, Institute of Biomedical Sciences, Academia Sinica, Taipei, Taiwan.

In Vivo Angiogenesis Assay.

All animal work was done under protocols approved by the Institutional Animal Care and Use Committee of the College of Medicine, National Taiwan University. The effect of peptides on in vivo angiogenesis was evaluated in the murine angiogenesis model using the Matrigel plug assay as described by Passaniti et al. (Passaniti A, et al., Lab Invest 1992, 67: 519-528).

In Vivo Tumorigenesis Assay.

CL1-5 cells ($2\times10^6$) were mixed with or without peptides and then implanted into the flanks of the 6-weekold SCID mice. Injected mice were examined every 5 or 7 days for tumor appearance, and tumor volumes were estimated from the length (a) and width (b) of the tumors, as measured with calipers, using the formula $V=ab^2/2$. Mouse experiments were approved by the Laboratory Animal Center, Institute of Biomedical Sciences, Academia Sinica.

Statistical Analyses.

All data are presented as the means and 95% confidence intervals (95% CI) of at least three experiments. All statistical analyses were done with the SAS Statistical Program (version 9.1; SAS Institute Inc.). Statistical significance was determined using an one-way ANOVA or as described. Fisher's exact test was done to test associations between covariates and NRP1 for categorical data, and Student's t test was used to test continuous variables. Survival curves were obtained by the Kaplan-Meier method. Disease-free and overall survival of patients with low versus high expression of NRP1 was analyzed using the log-rank test. Multivariate Cox proportional-hazards regression was done with overall or disease-free survival as the response variable. $P<0.05$ was considered statistically significant.

Example 1

NRP1 Expression Correlates with the Invasive Ability of Lung Cancer Cells

Five distinct lung tumor cell lines with progressive invasiveness were established previously. Microarray analysis showed that NRP1 was up-regulated in the highly invasive NSCLC cell lines, CL1-5 and CL1-5-F4 (FIG. 1A). NRP1 and its coreceptor VEGFR2 were only expressed in the highly invasive CL1-5 and CL1-5-F4 cells. Expression of the NRP1 ligand semaphorin 3A was down-regulated in an opposite pattern to NRP1. There were no differences in VEGF or plexin A1 expression in this cell panel (FIG. 1B).

Example 2

Figure 2:
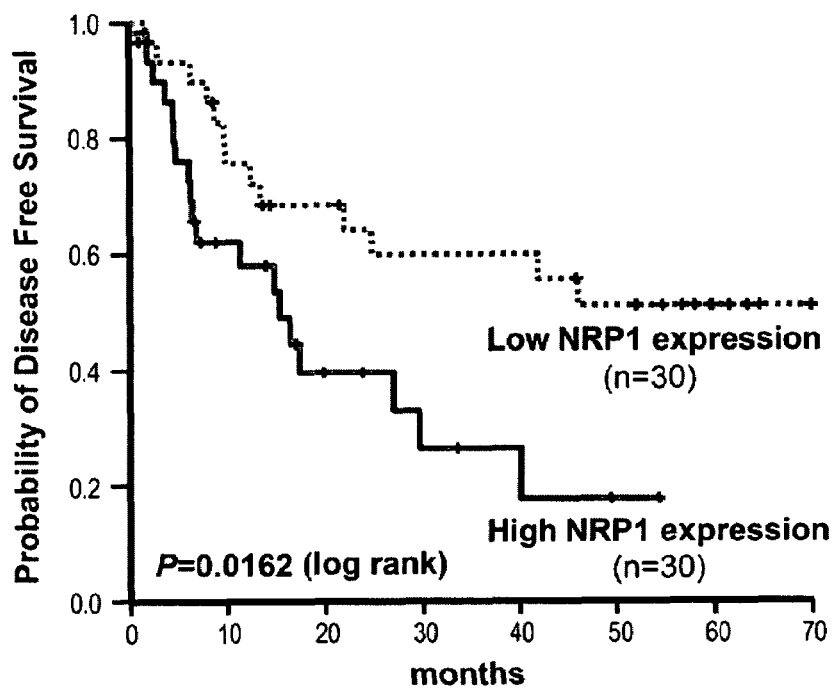
FIG. 2 shows Kaplan-Meier survival plots for patients with non-small cell lung cancer grouped according to NRP1 mRNA expression. The relative amount of tissue NRP1 mRNA, standardized against the amount of TATA-box binding protein mRNA, was expressed as $-\Delta C_T = [C_{T(NRP1)} - C_{T(TBP)}]$, where $C_T$ is the threshold cycle. Patients were included in the high-expression group when the $-\Delta C_T$ was 0.32 (the median) or greater. A: the difference in disease-free survival between the high- and low-expression patients was significant (P=0.0162). Tick marks: patients free of recurrence at their last follow-up. B: the difference in overall survival between the high- and low-expression patients was significant (P=0.0164). Tick marks: patients alive at their last follow-up. All statistical tests were two sided.
Figure 2:
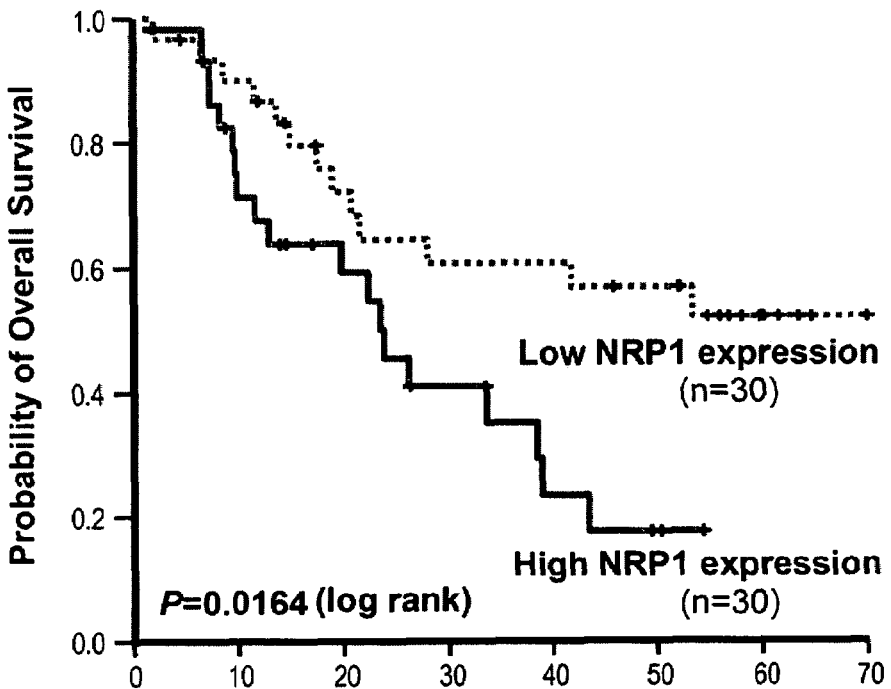

NRP1 mRNA Expression Correlates with Cancer Relapse and Survival in NSCLC Patients Real-time quantitative RT-PCR was used to determine the number of NRP1 transcripts in lung cancer tissues from 60 patients with NSCLC. We arbitrarily used the median value to classify patients into high- or low-expression groups. The clinicopathologic characteristics of the 60 NSCLC patients are shown in Table 1. Patients with high NRP1 expression had shorter disease-free (P=0.0162) and overall survival (P=0.0164) compared with low NRP1-expression patients (FIG. 2). Multivariate Cox's proportional hazards regression analyses showed that low NRP1 expression was associated with overall survival of NSCLC patients independent of clinicopathologic stage, age, sex, and cell type [0 for low and 1 for high NRP1 expression, respectively; hazard ratio (HR), 2.37; 95% CI, 1.15-4.9; P=0.0196]. Similarly, the hazard ratio for disease-free survival remained significant only for the expression of NRP1 (HR, 2.38; 95% CI, 1.15-4.91; P=0.0195).

Example 3

Endogenous NRP1 Expression Knockdown Suppresses Cancer Cell Invasion

Figure 3:
FIG. 3 shows suppression of NRP1 expression inhibited the invasion and migration abilities of CL1-5 cells. A: expression of NRP1 shown by Western blotting of tumor cells transfected by NRP1-siRNA-1, NRP1-siRNA-2, or nonsilencing siRNA. B: inhibition of CL1-5 cell-invasive activity by NRP1 siRNAs. The invasive activity of cells was detected by invasion assay. CL1-5 cells ($2.5 \times 10^4$) were seeded on Transwells coated with 30 µg Matrigel, transfected with NRP1-siRNA-1, NRP1-siRNA-2, or nonsilencing siRNA and incubated for 48 h. The cells that had invaded the membrane were then counted. Values were normalized to the relative invasion activity of the reagent control. Experiments were done in triplicate, three independent times. ANOVA revealed that the invasion ability was statistically significantly different among the cells treated with different concentrations of siRNAs, either siRNA-1 or siRNA-2 (siRNA-1 group, P<0.001; siRNA-2 group, P=0.002). C: inhibition of tumor cell migration by NRP1-siRNA determined by scratch wound healing assay. CL1-5 cells were transfected with siRNA-1 for 24 h, and cells were scratched with a yellow pipette tip. The wound was photographed after the scratch, and cell numbers were counted within the gap area. Pictures of a representative assay at 0, 18, 21, and 24 h are shown here. D: NRP1-siRNA inhibition of tumor cell migration at various times. The number of migrated cells within the gap area was counted after the scratch. Columns: mean of four independent experiments; bars: SE.*indicates P<0.05, which is significantly different from nonsilenced cells. E: sNRP1 inhibition of tumor cell invasion ability as shown by invasion assay. The relative invasion ability was statistically significantly different among the cells treated with different concentrations of sNRP1 by ANOVA (P=0.002). F: sNRP1 inhibition of F-actin polymerization and filopodia formation in CL1-5 cells. Red: F-actin.
Figure 3:
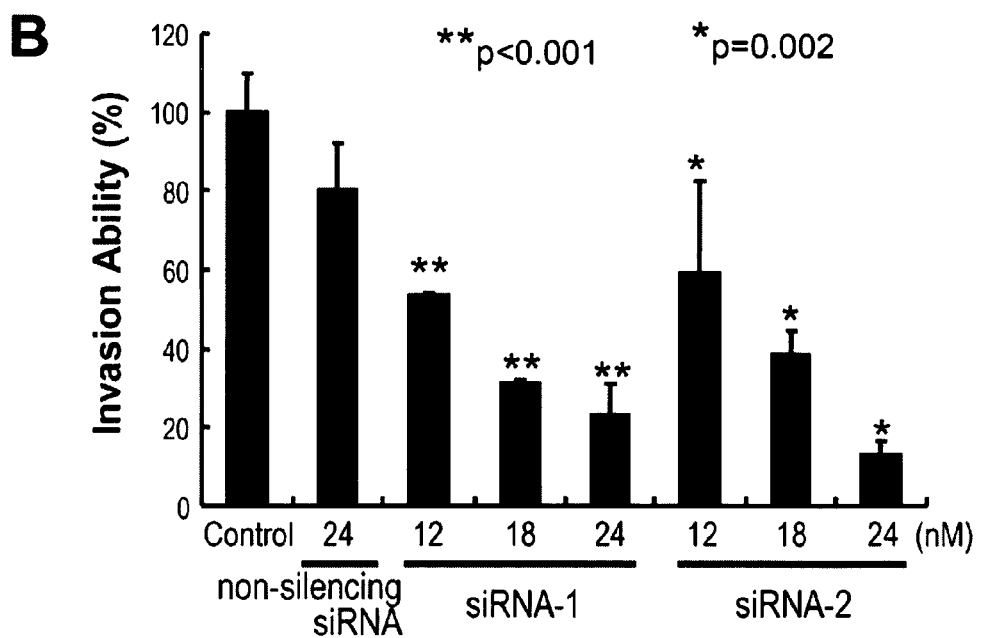
Figure 3:
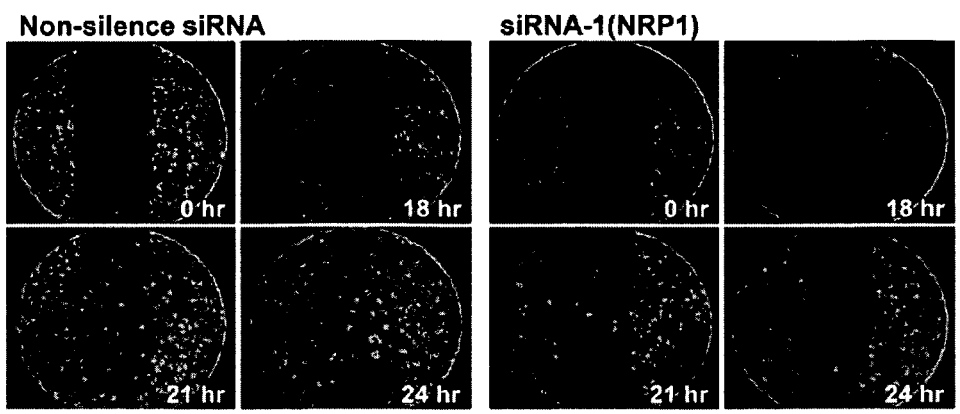
Figure 3:
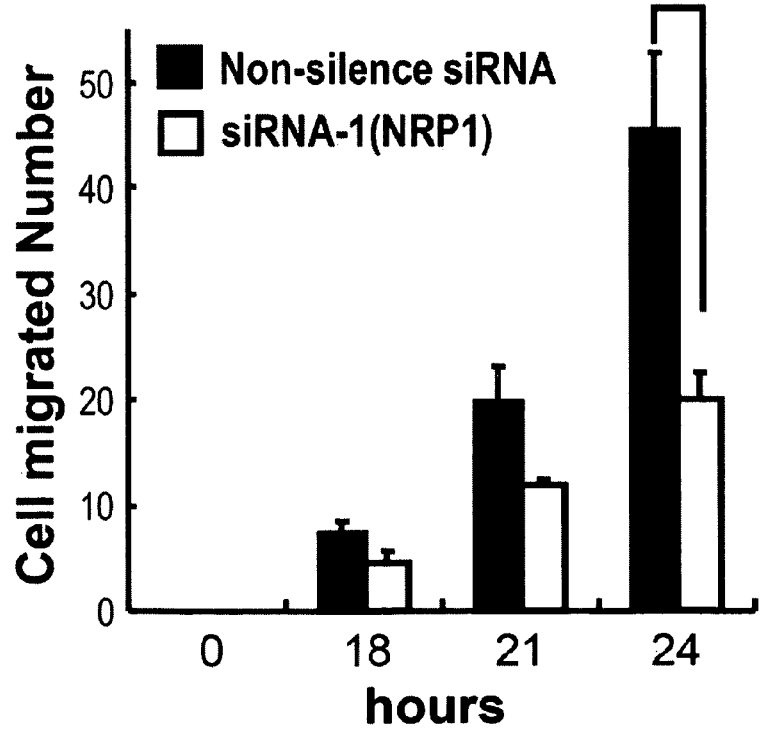
Figure 3:
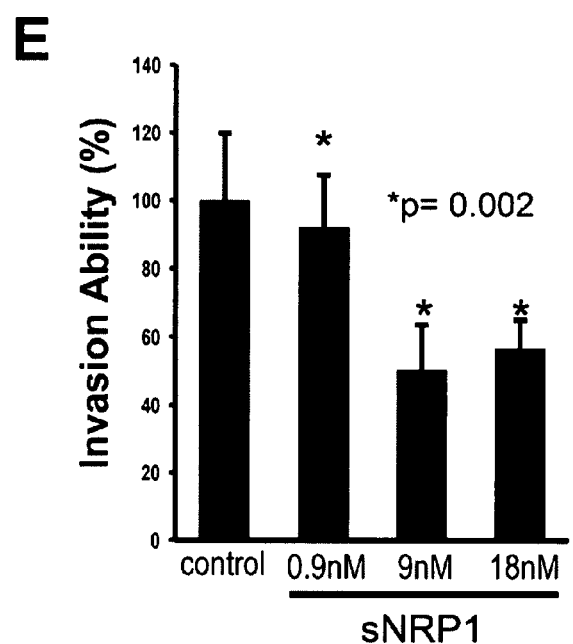
Figure 3:
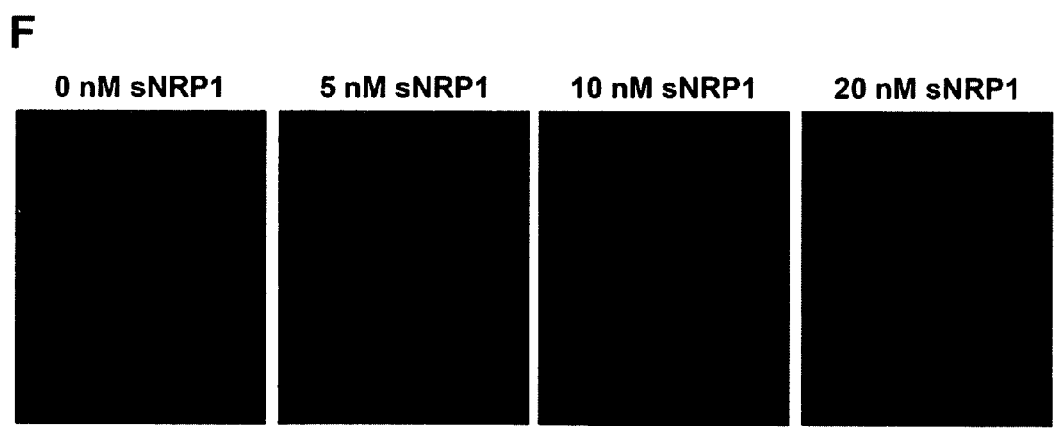
Figure 3:
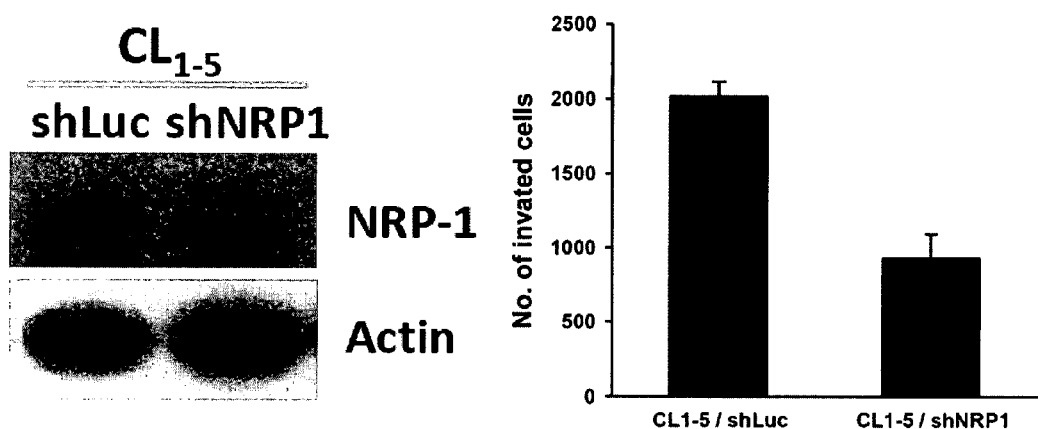
Figure 3:
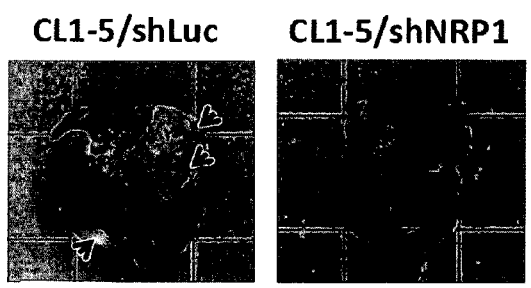
Figure 3:
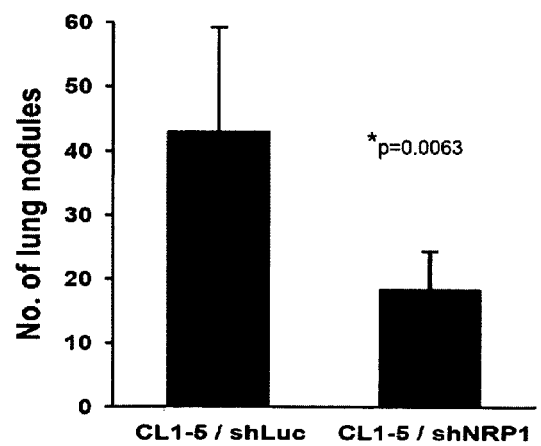

To knock down NRP1 expression, two individual siRNAs directed against the NRP1 gene were transfected into NRP1-positive lung cancer cells CL1-5. Significant suppression of NRP1 expression was achieved by siRNA-1 and siRNA-2 (FIG. 3A). Both NRP1 siRNAs decreased the invasion ability of CL1-5 cells in a dose-dependent manner compared with the nonsilencing siRNA control (FIG. 3B). To examine whether the anti-invasion activity of the NRP1-specific siRNAs is associated with suppression of cell mobility, the effects of NRP1-specific siRNA1 on the migration capability of cells were analyzed. CL1-5 cells were transfected with siRNA-1 or nonsilencing control siRNA; the migration ability was determined by the scratch wound healing assay. That NRP1 siRNAs can suppress CL1-5 cell mobility, and migration capability was shown by the scratch wound healing assay (FIG. 3C). NRP1-siRNAs significantly inhibited the migration of CL1-5 cells at 24 h (FIG. 3D).

Example 4

Soluble NRP1 Inhibits Cancer Cell Invasion and Filopodia Formation

Recombinant sNRP1 was expressed in human fibroblast (NIH-3T3) cells and was secreted into cultured medium sNRP1 proteins were purified from the conditioned medium by ammonium sulfate precipitation and then by Ni-NTA column purification on a fast protein liquid chromatography (FPLC) system. The binding affinity of the recombinant sNRP1 to $VEGF_{165}$ was determined by surface plasmon resonance analysis. The average dissociation constant (KD) of the human $VEGF_{165}$ binding to sNRP1 was 125 nmol/L, consistent with previous results obtained using the same technology (Dias S, et al., Proc Natl Acad Sci USA 2001, 98: 10857-10862). sNRP1 was expressed differently from intact NRP1 and seemed to be a $VEGF_{165}$ antagonist. There was a dose-dependent decrease in the invasion ability of CL1-5 cells after treatment with sNRP1 (FIG. 3E). The F-actin of CL1-5 cells was stained with rhodamineconjugated phalloidin and examined by fluorescence microscopy. sNRP1 inhibited F-actin polymerization and filopodia formation in CL1-5 cells in a dose-dependent manner (FIG. 3F).

Example 5

Knockdown of Endogenous NRP1 Expression Suppresses Cancer Metastasis In Vivo

Knockdown of endogenous NRP1 expression in CL1-5 cells by shRNA lentivirus significantly reduced the invasive activity by 50% (FIG. 3G). Mice injected with CL1-5/shNRP1 cells developed significantly fewer pulmonary metastatic nodules than those with CL1-5/shLuc cells (FIG. 3H).

Example 6

NRP1 Signaling Pathways Involve VEGFR2, PI3K, and Akt Activation

Figure 4:
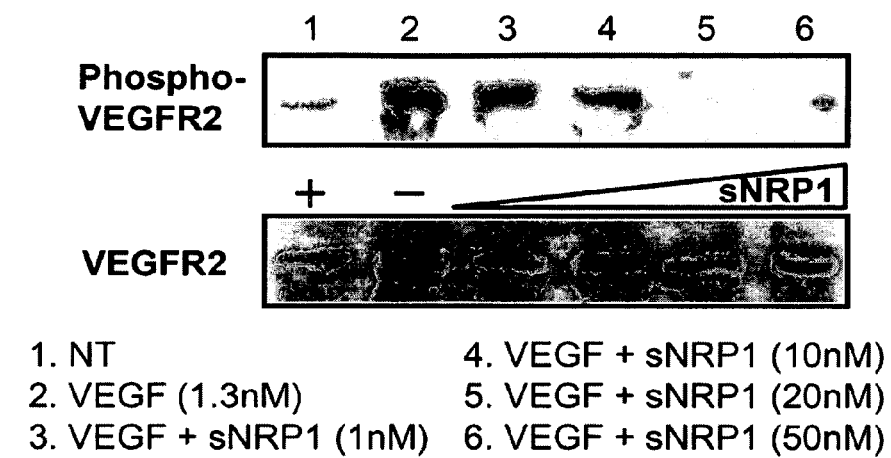
FIG. 4 shows that $VEGF_{165}$-induced NRP1 signaling involves VEGFR2 phosphorylation, activation of PI3K and Akt phosphorylation. A: sNRP1 inhibits phosphorylation of VEGFR2. Phosphorylation of VEGFR2 was determined by immunoprecipitation with an anti-VEGFR2 antibody followed by Western blotting with an anti-phospho-VEGFR2 antibody. Total VEGFR2 was determined by Western blot with an anti-VEGFR2 antibody. B: the effect of NRP1-siRNA on PI3K activity. After siRNA-1 (NRP1) transfection for 48 h, CL1-5 cells were treated in RPMI-SF medium with 1.3 nmol/$LVEGF_{165}$ for the indicated times. PI3K activity was detected as described in Materials and Methods. C: inhibition of Akt phosphorylation by sNRP1 in CL1-5 cells. CL1-5 cells were treated with 1.3 nmol/$LVEGF_{165}$ in the presence (a) or absence (b) of 10 nmol/L of sNRP1 for the indicated times. Akt and phosphorylated Akt proteins were detected by Western blotting. The ratio of phosphorylated to total Akt is represented by Akt-p/Akt. D: the invasion ability was statistically significantly different among the cells treated with different concentrations of wortmannin by ANOVA (P<0.001). E: the invasion ability was statistically significantly different among the cells treated with different levels of LY294002 by ANOVA (P<0.001).
Figure 4:
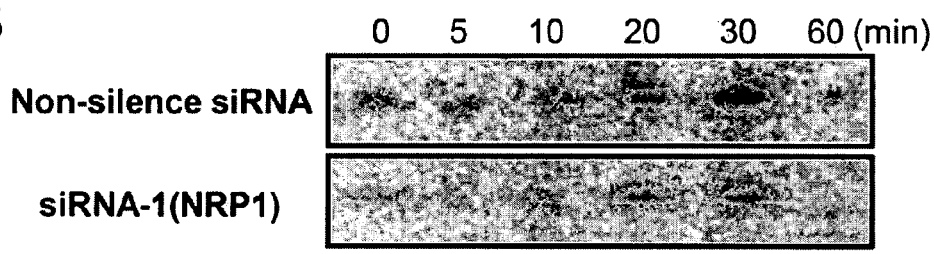
Figure 4:
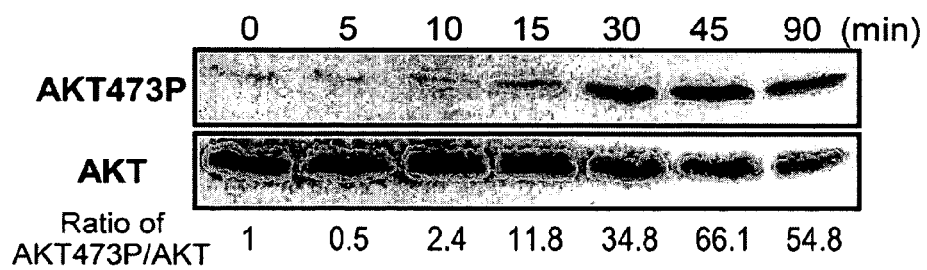
Figure 4:
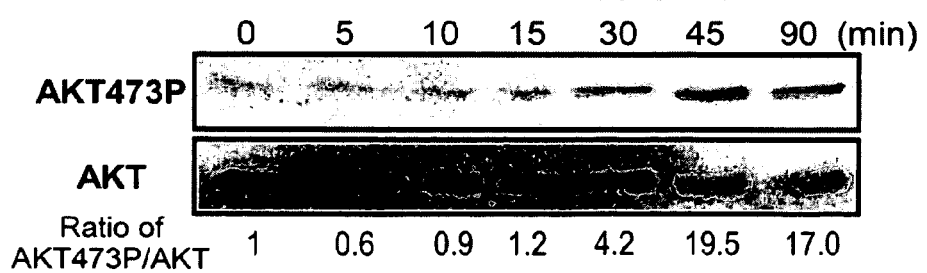
Figure 4:
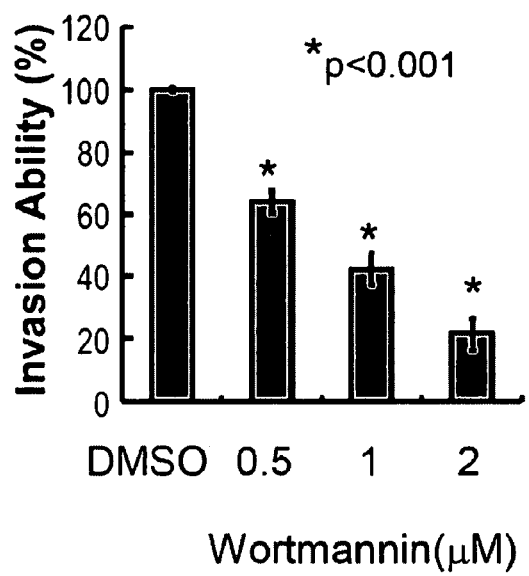
Figure 4:
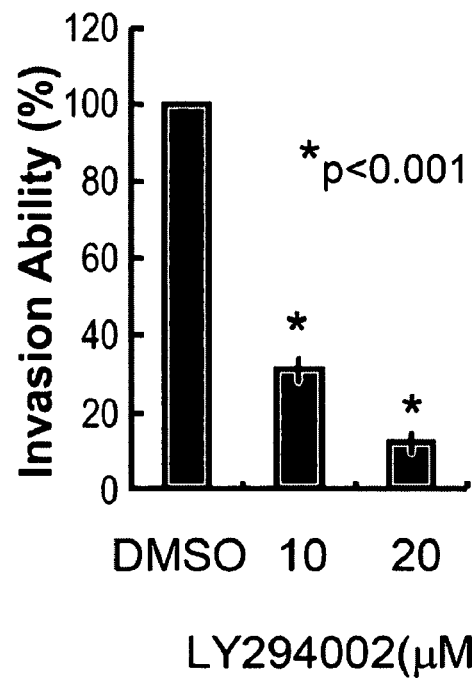

To identify the signaling pathways affected by NRP1, CL1-5 cells were treated with $VEGF_{165}$ for various periods and analyzed signaling intermediates. CL1-5 cells were treated with $VEGF_{165}$ and sNRP1, and the phosphorylation of VEGFR2 was determined by immunoprecipitation with an anti-VEGFR2 antibody followed by Western blotting with an anti-phospho-VEGFR2 antibody. $VEGF_{165}$-induced VEGFR2 activation was decreased by sNRP1 in a dose-dependent manner and was totally blocked by high concentrations of sNRP1 (FIG. 4A). $VEGF_{165}$ induced PI3K activation with peak phosphorylation at 30 min, which returned to the baseline levels by 60 min. The addition of siRNA-1 decreased $VEGF_{165}$-induced PI3K activation in CL1-5 cells compared with the nonsilencing siRNA-1 control (FIG. 4B). Phosphorylation of Akt, a downstream mediator of PI3K, is involved in NRP1 modulation of VEGF actions. $VEGF_{165}$-induced phosphorylation of Akt at Ser473 in CL1-5 cells was decreased to less than one third in the presence of sNRP1 (FIG. 4C). Both PI3K inhibitors, wortmannin and LY294002, decreased the invasion ability of CL1-5 cells (ANOVA: wortmannin, P<0.001; LY294002, P<0.001; FIGS. 4D and E).

Example 7

RRXR-Containing Peptides can Inhibit NRP1-Mediated VEGFR2 Phosphorylation

Figure 5:
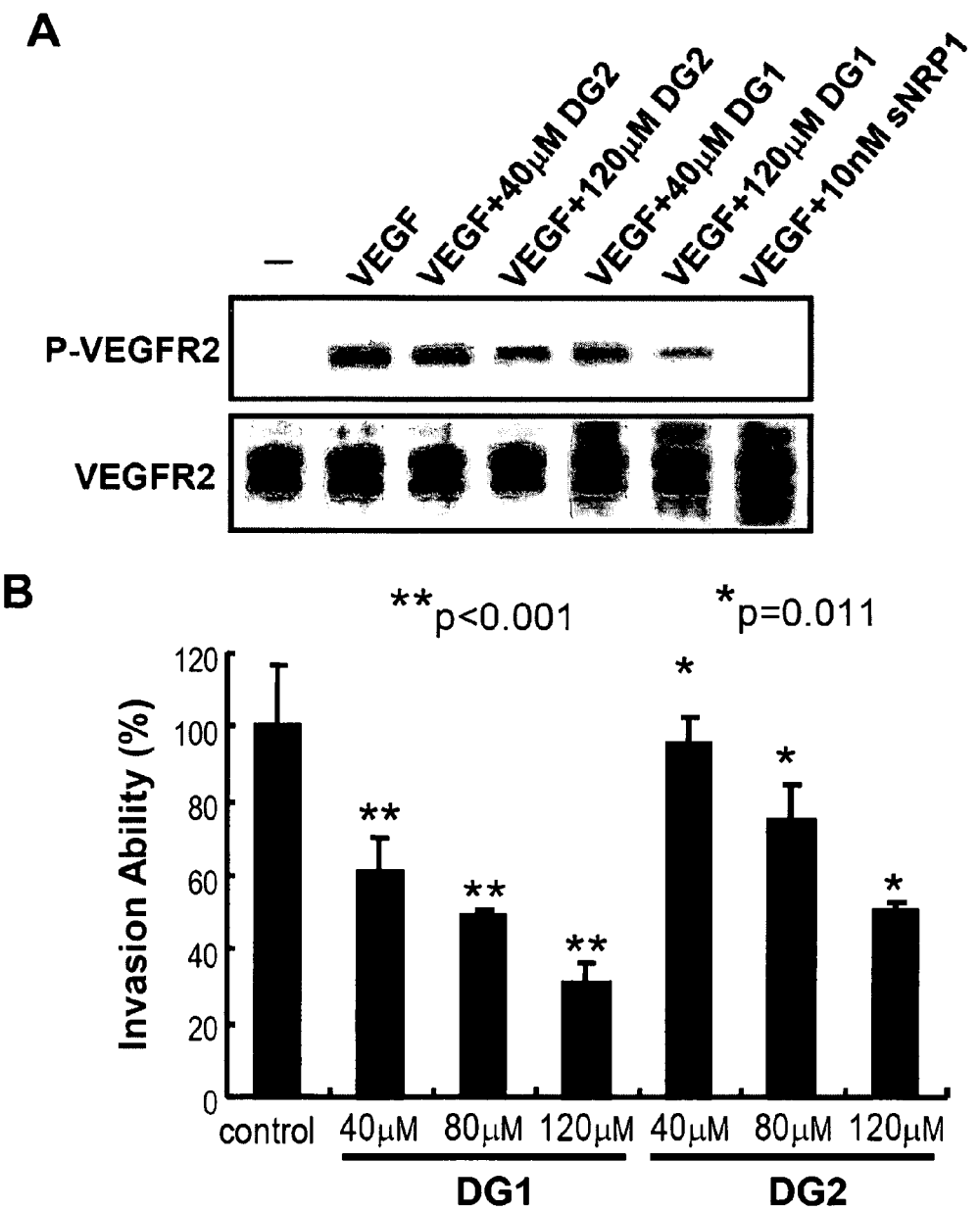
FIG. 5 shows cyclic 7-mer peptides bind NRP1 and inhibit CL1-5 invasion and angiogenesis in vivo. A: the selected peptides reduce phosphorylation of VEGFR2. HUVECs were pretreated with peptides for 10 min followed by treatment with VEGF for 5 min. Phosphorylation of VEGFR2 was determined by Western blotting with an anti-phospho-VEGFR2 antibody. Total VEGFR2 was determined by Western blotting with an anti-VEGFR2 antibody. B: the effect of peptides on CL1-5 cells invasive activity. The invasive activity of cells was detected by invasion assay. CL1-5 cells ($2.5 \times 10^4$) were seeded on Transwells coated with 30 μg matrigel and incubated with peptides DG1 or DG2 for 48 h.
Figure 5:
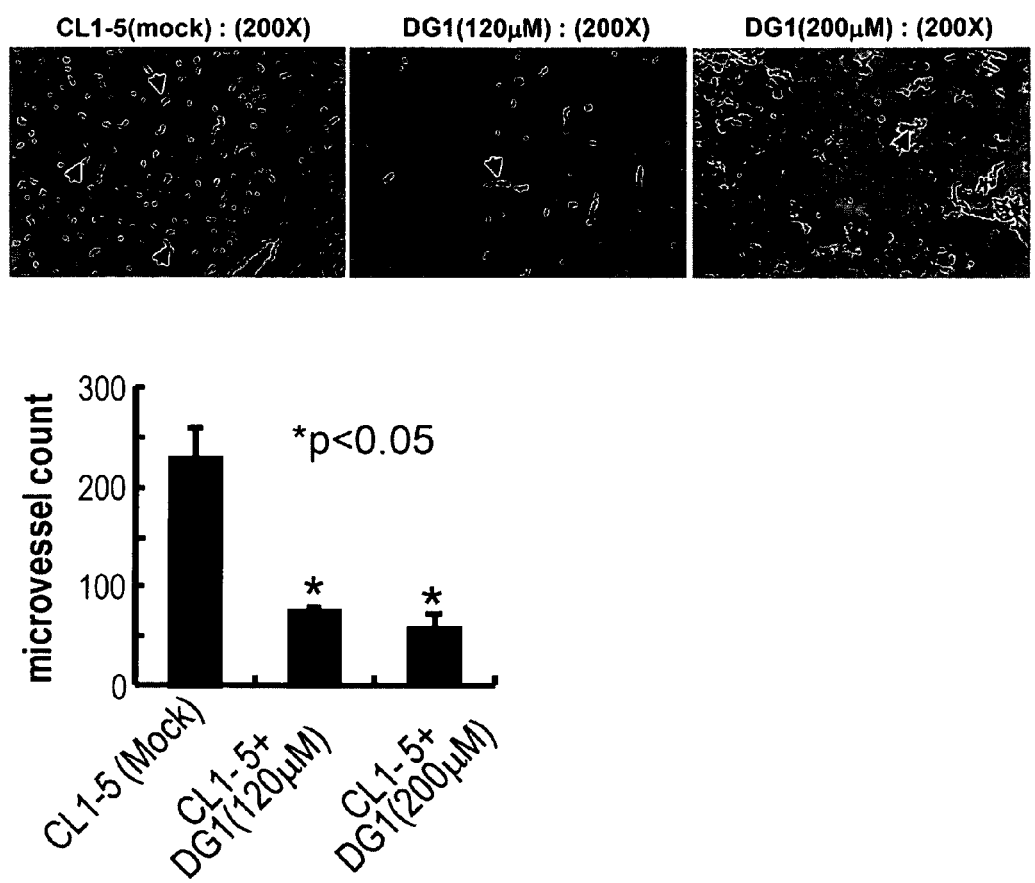
Figure 5:
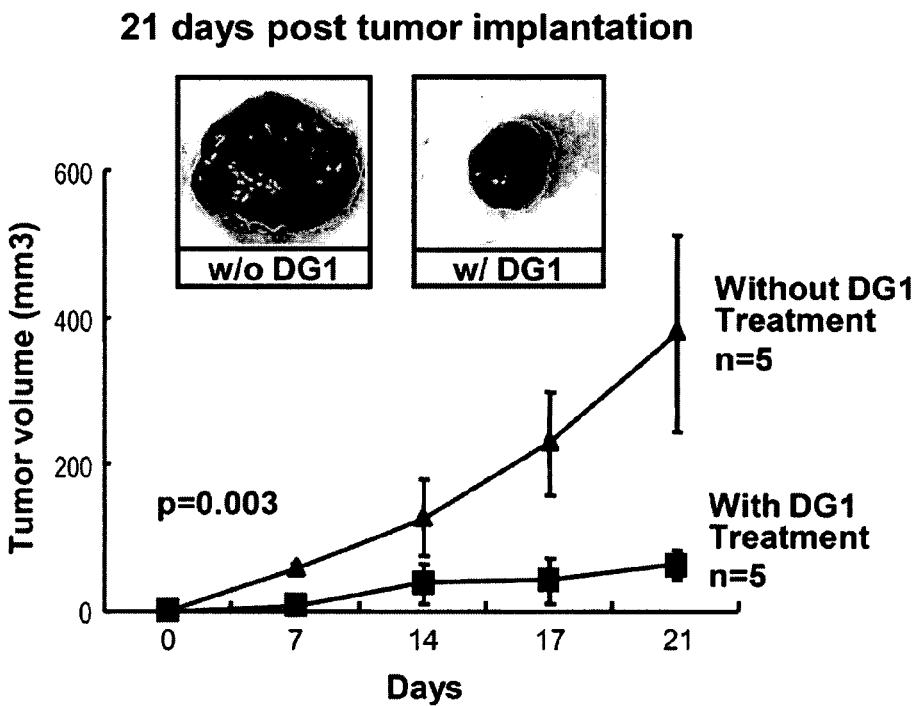
Figure 5:
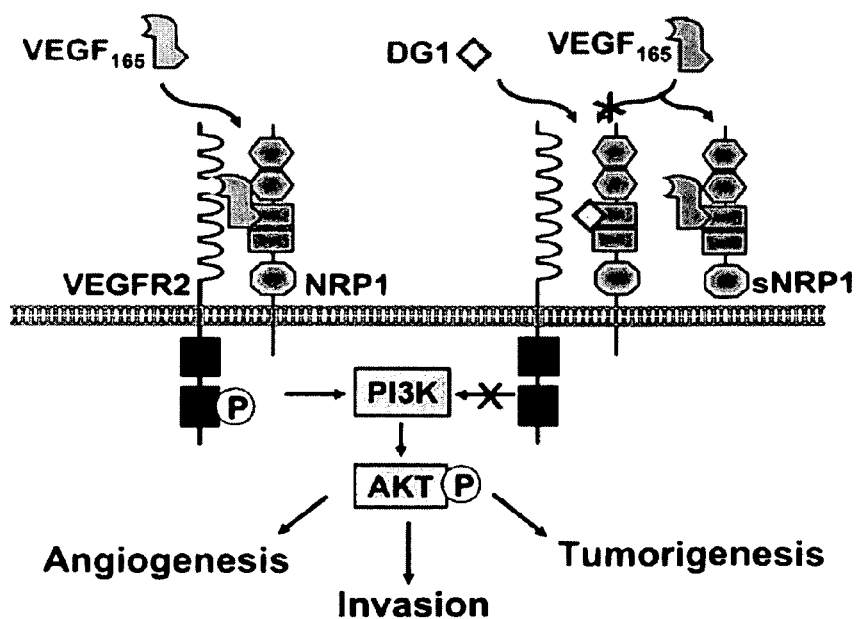

To identify whether any new signature motif can bind and inhibit NRP1-mediated invasion, mammalian cell-expressed NRP1 proteins were used as bait to screen a random cyclic 7-mer peptide library for NRP1-binding peptides. A Ph.D. C7C phage display library containing $10^{11}$ random cyclic 7-amino acid peptides was applied for biopanning. After four rounds of screening, 63 clones were isolated. DNA sequencing showed that almost all selected peptides contained arginine (R) residues. A consensus motif, -RRXR-, was found in nine clones by MULTALIN program alignment (Table 3). The two most potent peptides (cyclic 9-mer peptides, DG1, and DG2) were selected and chemically synthesized for further analysis of their binding kinetics and NRP1 inhibition. Surface plasmon resonance was used to measure the real-time association and dissociation of the binding of RRXR-containing peptides to NRP1. The average dissociation constants ($K_D$) for the binding of DG1 and DG2 to NRP1 were 1.40±0.23 and 5.37±0.49 μmol/L, respectively (Table 4). The slightly higher binding affinity of DG1 to NRP1 was due to a more favorable $k_a$. No binding was observed to either the immobilized VEGFR1 or VEGFR2 sensor chips (data not shown). DG1 and DG2 specifically inhibited $VEGF_{165}$-induced phosphorylation of VEGFR2 at $Tyr^{1214}$ in a concentration-dependent manner with a significant effect at 40 μmol/L and almost complete inhibition at 120 μmol/L (FIG. 5A).

TABLE 3

The RRXR motif of the peptides selected by binding to NRP1

| Peptide number | Sequence |
|---|---|
| 4-1 | R R P R M L T |
| 4-2 | Q L R R Q R R |
| 4-3 | H S R R M R K |
| 4-5 | R S R R I R L |
| 4-9 | M K R R P R K |
| 4-28 | R R L R R R R |
| 4-40 | P I R R Q R L |
| 4-43 | R R S R Q S R |
| 4-53 | H K R R I R Q |
| Consensus | - R R X R - |

TABLE 4

Kinetic constants for the interaction of the selected peptides with NRP1

| Peptide | $K_D$, μmol/L | $k_a$, $(mol/L)^{-1} s^{-1}$ | $k_d \times 10^{-4}$, $s^{-1}$ |
|---|---|---|---|
| DG1 | 1.40 ± 0.23 | 1,229 ± 246 | 17.2 ± 2.25 |
| DG2 | 5.37 ± 0.49 | 123.4 ± 24 | 6.63 ± 0.81 |

NOTE:
The kinetic constants were determined using the Blacore system as described in Materials and Methods.

Example 8

RRXR-Containing Peptides Inhibit Cancer Cell Invasion, Tumorigenesis, and Tumor Angiogenesis The in vitro invasion assay was done using the highly invasive CL1-5 cells to investigate the effects of DG1 and DG2 on the invasiveness of the lung carcinoma cells. Treatment with DG1 or DG2 peptides inhibited CL1-5 cell invasion in a dose-dependent manner (FIG. 5B). DG1 reduced the number of cancer cells invading through the Matrigel by 70%, and DG2 reduced the number of cancer cells by 50%. This suggests that the interaction of the peptides with NRP1 may be associated with NRP1-mediated cancer cell invasion. The treatment was not cytotoxic, suggesting that the decreased number of invading cells was due to the inhibitory effect of the RRXR-containing peptides on the invasive phenotype. To understand whether DG1 can reduce angiogenesis or tumorigenesis, in vivo angiogenesis and xenograft tumor assays were done. DG1 inhibited tumor angiogenesis in vivo (FIG.

5C). The tumor microvascular count from DG1-treated CL1-5 cells (75±4; in ×200 fields) was significantly less than that of the untreated tumor cells (227±33; in ×200 fields). The tumor angiogenesis activity of DG1-treated CL1-5 cells decreased significantly by 3-fold compared with the untreated tumor cells. The effect of DG1 on tumorigenicity in vivo was tested using the xenograft tumor assay. DG-1 treatment reduced tumor volume to 60.1 mm3 (95% CI, 27.6-92.6 mm$^3$) in mice 21 days after the inoculation of the CL1-5 cells, compared with the tumor volume of 464.1 mm$^3$ (95% CI, 200.1-728.2 mm3; P=0.003) without DG-1 treatment (FIG. 5D).

While the invention has been described and exemplified in sufficient detail for those skilled in this art to make and use it, various alternatives, modifications, and improvements should be apparent without departing from the spirit and scope of the invention.

What is claimed is:

1. A synthetic anti-NRP1 cyclic peptide for blocking NRP1 signaling pathways, consisting of SEQ ID NO: 1 or SEQ ID NO: 2.

2. A composition comprising the cyclic peptide of claim 1 and a pharmaceutical acceptable carrier.

* * * * *